(12) United States Patent
Prindle

(10) Patent No.: US 7,905,869 B2
(45) Date of Patent: Mar. 15, 2011

(54) DETECTABLE HEAVY DUTY NEEDLE

(75) Inventor: Gordon Prindle, Bartlett, IL (US)

(73) Assignee: Neogen Corporation, Lansing, MI (US)

( * ) Notice: Subject to any disclaimer, the term of this patent is extended or adjusted under 35 U.S.C. 154(b) by 0 days.

(21) Appl. No.: 10/215,339

(22) Filed: Aug. 8, 2002

(65) Prior Publication Data

US 2002/0193756 A1 Dec. 19, 2002

Related U.S. Application Data

(62) Division of application No. 09/714,041, filed on Nov. 16, 2000, now Pat. No. 6,488,668.

(51) Int. Cl.
*A61M 25/00* (2006.01)
*A61M 5/32* (2006.01)

(52) U.S. Cl. ........................................ 604/272; 604/264

(58) Field of Classification Search .............. 604/27, 604/181, 187, 188, 240, 241, 264, 272, 506, 604/529, 533, 905; 452/52, 65–67, 69, 198; 128/897–899; 119/174; 324/202.22
See application file for complete search history.

(56) References Cited

U.S. PATENT DOCUMENTS

| | | | | |
|---|---|---|---|---|
| 3,179,107 | A | * | 4/1965 | Clark ............................ 604/242 |
| 3,741,198 | A | | 6/1973 | Burton |
| 3,780,734 | A | | 12/1973 | Wulff |
| 3,865,644 | A | * | 2/1975 | Hellner et al. .................. 420/47 |
| 3,882,849 | A | * | 5/1975 | Jamshidi ........................ 600/566 |
| RE28,713 | E | | 2/1976 | Stevens et al. |
| 4,335,718 | A | * | 6/1982 | Calabrese ..................... 604/272 |
| 4,490,139 | A | * | 12/1984 | Huizenga et al. ............... 604/57 |
| 4,508,119 | A | | 4/1985 | Tukamoto |
| 4,526,177 | A | | 7/1985 | Rudy |
| 4,702,737 | A | | 10/1987 | Pizzino |
| 4,734,643 | A | | 3/1988 | Bubenik et al. |
| 4,747,834 | A | | 5/1988 | Prindle |
| 4,774,741 | A | | 10/1988 | Bernharadt |
| 4,788,844 | A | | 12/1988 | Summers |
| 4,969,963 | A | | 11/1990 | Honkura et al. |

(Continued)

FOREIGN PATENT DOCUMENTS

CA 2298277 8/2001

(Continued)

OTHER PUBLICATIONS

Becker, Neil H. et al, Residue Avoidance Program—Injection Techniques for Swine, Nov. 1985, University of Kentucky College of Agriculture Website.*

(Continued)

*Primary Examiner* — Nicholas D Lucchesi
*Assistant Examiner* — Victoria P Campbell
(74) *Attorney, Agent, or Firm* — Ian C. McLeod; Steven M. Parks

(57) ABSTRACT

The present invention provides a detectable heavy duty needle cannula (12) for use in hypodermic syringes and the like. Needle cannula (12) comprises a magnetizable or magnetized stainless steel alloy, which enables needle cannula (12) to be detectable in metal detectors that are commonly used in the meat processing industry to detect broken needle cannulas in the flesh of slaughtered animals. Needle cannula (12) further comprises a sidewall (17) that is thicker than the sidewalls of prior art needle cannulas. The thicker sidewall imparts to needle cannula (12) greater resistance to breakage during the process of injecting animal health products into an animal and greater detectability in a metal detector.

18 Claims, 3 Drawing Sheets

U.S. PATENT DOCUMENTS

| | | | |
|---|---|---|---|
| 5,015,235 A | | 5/1991 | Crossman |
| 5,026,355 A | | 6/1991 | Sweeney et al. |
| 5,041,098 A | * | 8/1991 | Loiterman et al. ............ 604/175 |
| 5,165,218 A | | 11/1992 | Callahan |
| 5,336,186 A | | 8/1994 | Haber |
| 5,372,778 A | * | 12/1994 | Yahagi et al. ................... 420/41 |
| 5,411,613 A | | 5/1995 | Rizk |
| 5,512,237 A | | 4/1996 | Stigenberg |
| 5,527,283 A | | 6/1996 | Swisher |
| 5,601,664 A | | 2/1997 | Kosa et al. |
| 5,649,546 A | | 7/1997 | Steinbeck |
| 5,715,822 A | | 2/1998 | Watkins |
| 5,720,300 A | | 2/1998 | Fagan |
| 5,792,180 A | | 8/1998 | Munoz |
| 5,879,333 A | * | 3/1999 | Smith ...................... 604/164.04 |
| 5,894,015 A | | 4/1999 | Rechtin |
| 5,900,126 A | | 5/1999 | Nelson et al. |
| 5,923,165 A | | 7/1999 | Horita et al. |
| 5,951,788 A | | 9/1999 | Holmberg |
| 6,027,482 A | | 2/2000 | Imbert |
| 6,211,789 B1 | | 4/2001 | Oldham |
| 6,238,491 B1 | | 5/2001 | Davidson et al. |
| 6,599,276 B1 | * | 7/2003 | Humphrey ................... 604/272 |

FOREIGN PATENT DOCUMENTS

| | | |
|---|---|---|
| EP | 0 279 583 A2 | 2/1988 |
| EP | 0 806 683 A2 | 4/1997 |
| EP | 0 899 589 A2 | 3/1999 |
| WO | WO 93/07303 | 4/1993 |

OTHER PUBLICATIONS

Mironova, N. S., Quality of Injection Needles, Dec. 1970, Consultants Bureau, Plenum Publishing Corporation.*

American Journal of Veterinary Research publication entitled "Breakage and Deformation Characteristics of Hypodermic Devices Under Static and Dynamic Loading." vol. 60, No. 3, pp. 292-298. Mar. 1999.

Farmscape News. May 1, 2000 (Episode 419-New Needle Promices to Reduce Risk of Needle Fragments in Meat); David Wasylyshen-Canada Pork International.

Article entitled "Report on the Beef Industry Broken Needle Testing—A Comparison of PDN and Monoject Needles" by J.L. Aalhus & D. Best (Lacombe Research Centre); D. Wasylyshen (Canada Pork International); D. Pedersen & S. Craig (Loma International). Jun. 30, 2000.

Farmscape News. Aug. 1, 2000 (Episode 484-Tests Prove New Hypodermic Needle to be Highly Detectable in Meat); Grant Humphrey—Process Detectable Needles.

Western Producer article entitled "Sound of Alarm Bell Music to Inventor" by Roberta Rampton. Aug. 10, 2000.

Western Producer article entitled "Marketer Takes Needle Challenge" by Robert Rampton. Aug. 10, 2000.

Farmscape News. Aug. 23, 2000 (Episode 499-CQA Officials Endorse New Hypodermic Needle); Dawn LeBlanc-Canada Pork Council.

Schering-Plough News Release entitled "Schering-Plough Animal Health Corporation Signs Agreement With Canadian Firm to Market Highly Detectable Needles in North America". Feb. 25, 2001.

ASTM International standard (Designation: A789/A 789M-02a) entitled "Standard Specification for Seamless and Welded Ferritic/Austenitic Stainless Steel Tubing for General Service" published Dec. 2002.

ISO Standard No. 9626; 1991.

* cited by examiner

DETECTABLE HEAVY DUTY NEEDLE

CROSS-REFERENCE TO RELATED APPLICATION

This is a divisional of application Ser. No. 09/714,041, filed Nov. 16, 2000, now U.S. Pat. No. 6,488,668.

STATEMENT REGARDING FEDERALLY SPONSORED RESEARCH OR DEVELOPMENT

Not Applicable.

BACKGROUND OF THE INVENTION (1) Field of the Invention

The present invention relates to a detectable heavy duty needle cannula for use in hypodermic syringes and the like. The needle cannula comprises a magnetized stainless steel alloy, which enables the needle cannula to be detectable in metal detectors that are commonly used in the meat processing industry to detect broken needle cannulas in the flesh of slaughtered animals. The needle cannula further comprises a sidewall that is thicker than prior art needle cannulas. The thicker sidewall imparts to the needle cannula greater resistance to breakage during the process of injecting animal health products into an animal and greater detectability in a metal detector.

(2) Description of Related Art

Stainless steel alloys are extensively used in manufacturing needle cannulas for hypodermic syringes for injecting animal health products into animals. From time to time, when these needles are used to vaccinate an animal, particularly the large domestic animals used for meat production, a part of the needle cannula breaks off and remains lodged within the flesh of the animal. Because meat containing a broken piece of needle is unfit for human consumption, any meat that contains a broken needle must be separated from the meat that is safe for human consumption.

The meat processing industry uses metal detectors to detect broken needles lodged within the flesh of the animal. However, because the needle cannulas used for veterinary purposes are made from non-magnetic stainless steel alloys, they are difficult to detect with the metal detectors that are used in the meat processing industry. Detection is particularly difficult when the needle's length to diameter ratio is low because at such low ratios the orientation of the needle in the meat affects detectability.

In order to improve detection of these needles, the metal detectors are routinely operated at high sensitivity levels. However, at sensitivity levels the frequency of false positives is increased. Therefore, a greater proportion of meat than is necessary is culled.

Therefore, there is a need for a needle cannula that is more resistant to breakage during the process of injecting animal health products into an animal. There is also a need for a needle cannula that can be readily detected in the metal detectors that are commonly used in the meat processing industry to detect broken needle cannula in the flesh of animals after slaughter.

SUMMARY OF THE INVENTION

The present invention provides a detectable heavy duty needle cannula for use in hypodermic syringes and the like. The needle cannula comprises a magnetic stainless steel alloy, which enables the needle cannula to be detectable in a metal detector. Particularly in the metal detectors that are commonly used in the meat processing industry to detect broken needle cannulas in the flesh of slaughtered animals. The needle cannula further comprises a sidewall that is thicker than prior art needle cannulas, which imparts to the needle cannula greater resistance to breakage during the process of injecting animal health products into an animal and increases its detectability in a metal detector.

The present invention provides a needle assembly comprising an elongate permanently magnetizable or magnetic stainless steel needle cannula having a proximal end, a distal end and a sidewall therebetween, the cannula having a lumen therethrough wherein the cannula at its proximal end is securely fixed to a mounting hub which is capable of being mounted on a device for injecting a dosage of a material in an animal. In particular, a needle assembly for use in a hypodermic needle and the device is a hypodermic syringe. Preferably, the sidewall has a thickness greater than 0.46 mm, in particular when the lumen has a diameter of about 1.19 mm. In a preferred embodiment, the needle cannula has a circular cross-section and the mounting hub includes projections extending therefrom for threaded engagement with a luer collar.

The present invention also provides a stainless steel tubular needle defined by at least one wall forming the tube and supported on a hub for mounting on a device for injecting a dosage of a material in an animals, wherein the needle is magnetizable or magnetic to a level which enables detection of the magnetism of the needle when broken off in the flesh of an animal when the animal is slaughtered and processed. Preferably, the needle is a hypodermic needle and wherein the material is a fluid. It is further preferable that the wall have a thickness of greater than 0.018 inch and an inside diameter of about 0.046 inch. It is preferable further still that the needle have a circular cross-section.

The present invention also provides a method of injecting flesh of a living food animal which comprises (a) providing an injection means comprising a tubular needle defined by at least one wall forming the tube and supported on a hub and mounted on a device for injecting a dosage of a material in an animal, wherein the needle is made of stainless steel, which is magnetizable or magnetic at a level that enables detection of the magnetism of the needle if the needle is broken off in the flesh of the living animal during the injection; and (b) injecting the living animal with the dosage using the needle, whereby when the needle breaks in the animal during the injection, the needle can be detected in the flesh of the animal upon slaughter and processing into the food.

The present invention further provides in a slaughtering method for slaughter and processing of animals for food while conveying the flesh of the animal, the improvement which comprises detecting a broken stainless steel tubular needle in the flesh, wherein the needle has at least one wall and is supported on a hub for mounting on a device for injecting a dosage of a material into an animal, wherein the needle is magnetized to a level which enables detection of the magnetism of the needle when broken off in the flesh of an animal when the animal is slaughtered and processed. In the foregoing methods it is preferable that the needle be a hypodermic needle. Particularly, a needle wherein the wall has a thickness of greater than 0.018 inch, and further, wherein the needle has an inside diameter of about 0.046 inch. The method is particularly useful when the animal is a swine.

In either of the above methods, the needle can be the above permanently magnetizable or magnetic stainless steel needle cannula having a proximal end, a distal end and a sidewall therebetween, the cannula having a lumen therethrough defining a cannula longitudinal axis wherein the cannula at its proximal end is securely fixed to a mounting hub which is capable of being mounted on a device for injecting a dosage of a material in an animal.

In any one of the aforementioned embodiments of the present invention, the stainless steel comprises Fe and 0.01-3.0 wt % Si, less than 0.03 wt % P, 4-25 wt % Cr, 0.003-7.0 wt % Al, 0.01-1.0 Mn, 0.001-0.03 wt % S, 0.01-5.0 wt % Mo, 0.01-1.0 wt % Ti, 0.003-0.08 wt % C, 0.01-5.0 wt % Ni, 0.01-0.5 wt % Cu, less than 0.01 wt % Pb, 0.02-0.5 Bi, 0.5-1.0 wt % Nb, 0.02-1.0 wt % Zr, and 0.05-1.0 wt % V. Preferably, a stainless steel alloy comprising Fe and 0.36 wt % Si, 0.02 wt % P, 24.68 wt % Cr, 0.01 wt % Al, 0.90 wt % Mn, 0.009 wt % S, 1.80 wt % Mo, less than 0.01 wt % Ti, 0.08 wt % C, 4.98 wt % Ni, 0.10 wt % Cu, and less than 0.01 wt % Pb.

Therefore, it is an object of the present invention to provide a needle cannula that is more resistant to breakage during the process of injecting animal health products into an animal.

It is also an object of the present invention to provide a needle cannula comprising a stainless steel alloy that is magnetized to facilitate detection of the broken needle cannula in the flesh of the animal using the metal detectors that are commonly used in the meat processing industry.

These and other objects will become increasingly apparent with reference to the following descriptions and the drawings.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

The present invention provides a detectable heavy duty needle cannula for use in hypodermic syringes, catheters, and the like. The needle cannula comprises a magnetized stainless steel alloy, which enables the needle cannula or broken pieces of the needle cannula in the flesh of an animal to be detected in a metal detector regardless of the orientation of the broken piece in the flesh. Preferably, the needle cannula comprises a permanently magnetized stainless steel alloy. The present invention is particularly useful to the meat processing industry because it enables broken needle cannulas in the flesh of slaughtered animals to be detected using the metal detectors already being used. The present invention does not require the meat processing industry to purchase new metal detectors. The needle cannula of the present invention further comprises a sidewall that is thicker than prior art needle cannulas, which imparts to the needle cannula greater resistance to breakage during the process of injecting animal health products into an animal.

Thus, the needle cannula of the present invention is more resistant to breakage than the thinner prior art needles and because of both its thickness and magnetizability it is easier to detect a broken piece of the needle in the flesh of an animal during processing of the animal after slaughter. Furthermore, the needle cannula of the present invention is magnetizable while still comprising a stainless steel alloy, which makes it acceptable for administering animal health products to an animal.

Figure 1:
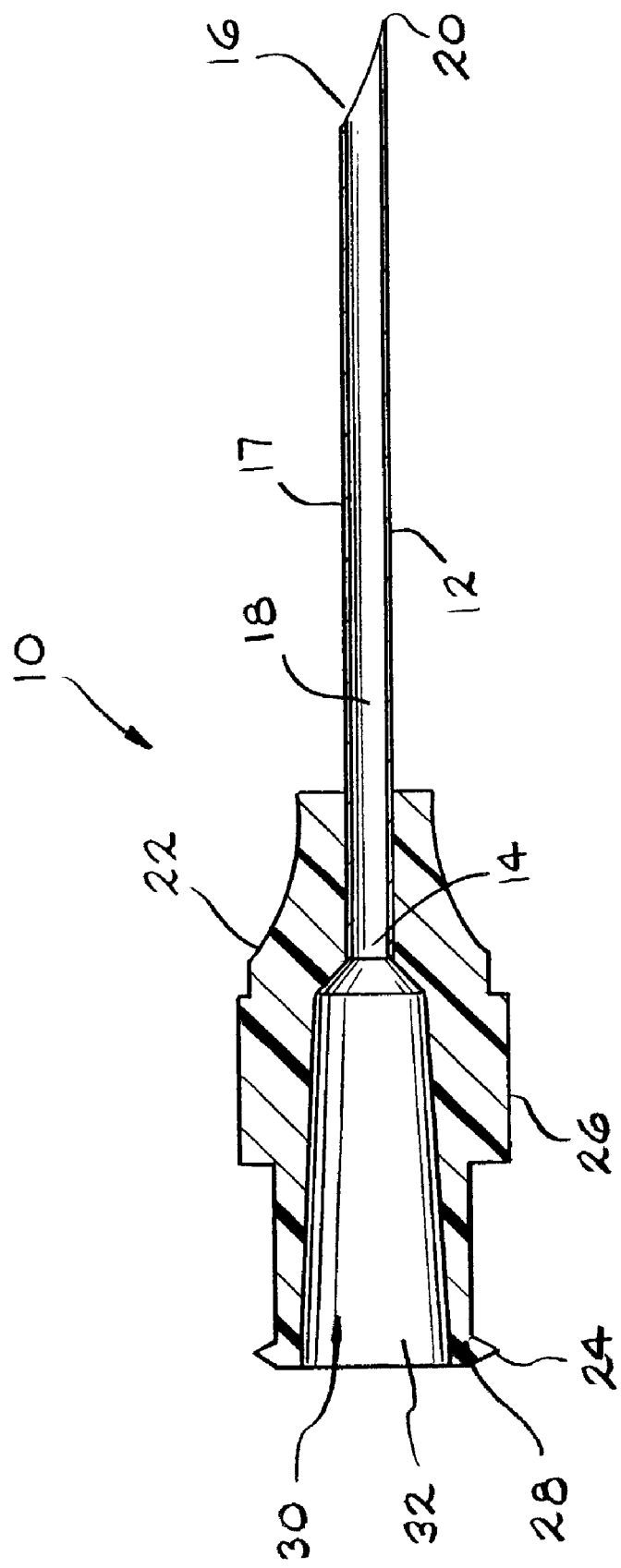
FIG. 1 is a longitudinal cross-sectional view of the needle assembly comprising the detectable heavy duty needle of the present invention.

FIG. 1 schematically illustrates a needle assembly 10 adapted for detachably mounting on a luer collar of a hypodermic syringe or the like comprising the detectable heavy duty needle cannula 12 having proximal end 14, distal end 16, and a sidewall 17 with an outer sidewall 17A and inner sidewall 17B therebetween having a lumen 18 extending therethrough defining a longitudinal axis. Distal end 16 of the needle cannula 12 preferably includes sharpened tip 20. A mounting hub 22 is securely affixed to the proximal end 14 of needle cannula 12 and includes projections 24 extending therefrom for threaded engagement with a luer collar or like attachment means. Thus, needle assembly 10 is mountable on a hand-held hypodermic syringe barrel. However, needle assembly 10 can also be mounted on a catheter device or mounted on automatic injection devices.

The mounting hub 22, preferably metal such as a stainless steel alloy or brass alloy or molded polypropylene plastic or the like, is comprised of a main body section 26 which has a means for fixedly retaining needle cannula 12 associated therewith and an axially extending rigid wall section 28 adapted for detachably engaging a hypodermic syringe outlet (not shown). The mounting hub 22 has an axial passage 30 which extends longitudinally through the end walls of mounting hub 22. The distal portion 32 of axial passage 30 preferably has a diameter slightly larger than the outer diameter of a male discharge outlet of a syringe on which the needle assembly 10 is adapted to be mounted. The outer surface 34 of mounting hub 22 can be provided with flat surfaces to serve as gripping means to facilitate mounting needle assembly 10 on an outlet of a hypodermic syringe or the like. Alternatively, mounting hub 22 can be provided with one or more radially extending projections to serve as the gripping means.

Figure 2:
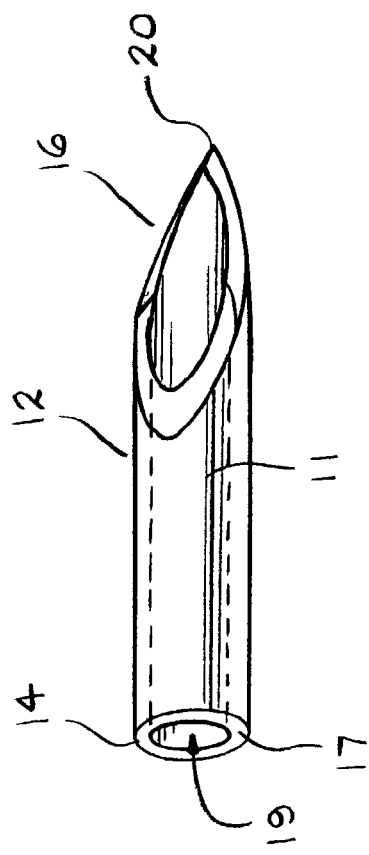
FIG. 2 is an isometric view of the detectable heavy duty needle of the present invention.

As shown in FIG. 2 in greater detail, needle cannula 12 is tubular with proximal end 16, distal end 14, and a sidewall 17 therebetween. The needle cannula 12 has a lumen 18 defining a cannula longitudinal axis 19. Preferably, needle 12 has a sharpened tip 20 at distal end 16 and is blunt at proximal end 14. In the case of the 16 gauge embodiment of the needle of the present invention, the sidewall 17 has a thickness greater than 0.46 mm (0.018 inch), preferably a thickness of 0.64 mm (0.025 inch) and the diameter of lumen 18 is about 1.19 mm (0.047 inch). Thus, the outer diameter of needle 12 is about 1.8 mm (0.072 inch). Preferably, the needle cannula of the present invention has a circular cross-section. In contrast, a 16 gauge prior art needle has an outside diameter of about 1.65 mm (0.065 inch) and a lumen diameter of about 1.19 mm (0.047 inch). Therefore, the wall of the prior art needle is about 0.46 mm (0.018 inch), which is somewhat more likely to break. Also, because the prior art needle cannula has a smaller diameter, a broken piece of the prior art needle cannula is less detectable. FIG. 1 shows a particular embodiment of needle assembly 10 comprising needle cannula 12; however, the detectable needle cannula of the present invention is not limited to that particular embodiment. As would be apparent to one skilled in the art, needle cannula 12 can comprise other needle assembly embodiments such as the needle assembly embodiments shown in U.S. Pat. RE No. 28,713 to Stevens et al. and U.S. Pat. No. 6,027,482 to Imbert.

While the 16 gauge embodiment is shown herein, the needle cannula of the present invention includes needle cannulas of other gauges and needle assemblies comprising needle cannulas of other gauges. For example, needle cannulas that are useful for medical and veterinarian purposes generally include those gauges within the range 14 to 26. Thus, the needle cannula of the present invention includes, but is not limited to, gauges between 14 and 27. It should be understood that because the sidewall of the needle cannula of the present invention is thicker than the sidewall of prior art needle cannulas and the outer diameter of the needle cannula determines the gauge, a 16 gauge needle cannula of the present invention has an outer diameter similar to the outer diameter of a 15 gauge needle cannula.

The detectable heavy duty needle cannula of the present invention comprises a magnetized stainless steel alloy. The stainless steel alloy can comprise any corrosion-resistant magnetic material with an elemental composition within the range set forth in U.S. Pat. No. 5,601,644 to Kosa et al and U.S. Pat. No. 4,969,963 to Honkura et al. In general, the magnetized stainless steel comprises 0.01-3.0 wt % Si, less than 0.03 wt % P, 4-25 wt % Cr, 0.003-7.0 wt % Al, 0.01-1.0 Mn, 0.001-0.03 wt % S, 0.01-5.0 wt % Mo, 0.01-1.0 wt % Ti, 0.003-0.08 wt % C, 0.01-5.0 wt % Ni, 0.01-0.5 wt % Cu, less than 0.01 wt % Pb, and the remainder Fe. Preferably, instead of Pb, the magnetized stainless steel comprises 0.02-0.5 Bi. Preferably, the magnetic stainless steel further comprises 0.5-1.0 wt % Nb, 0.02-1.0 wt % Zr, and 0.05-1.0 wt % V, which improve the toughness and magnetic properties of the stainless steel. In a preferred embodiment, the magnetized stainless steel comprises, based on a chemical test where the test results conform to UNS S32900, 0.36 wt % Si, 0.02 wt % P, 24.68 wt % Cr, 0.01 wt % Al, 0.90 wt % Mn, 0.009 wt % S, 1.80 wt % Mo, less than 0.01 wt % Ti, 0.08 wt % C, 4.98 wt % Ni, 0.10 wt % Cu, and less than 0.01 wt % Pb. The remainder comprises Fe.

Thus, the preferred stainless steel alloy is an alloy that is permanently magnetic or magnetizable before detection. The magnetic alloy is detectable using the metal detectors that are commonly used in the meat processing industry. Thus, the meat processing industry does not need to purchase new equipment for detecting the needle cannulas of the present invention or pieces thereof in the flesh of animals or their meat products. However, the present invention is not limited to needle cannulas comprising stainless steel alloys that are permanent magnets.

Alternatively, the needle cannula of the present invention can comprise a stainless steel alloy that is not a permanent magnetic but is capable of being magnetized in a magnetic field to maintain a residual magnetism. When the alloy is subjected to a high magnetic field, preferably of an intensity equivalent to or greater than required for imparting saturated magnetization, the alloy acquires a residual magnetism that persists when the magnetic field is removed. Thus, a needle cannula or piece thereof comprising a residual magnetism, which is embedded in the flesh of an animal or meat product, can be detected in a metal detector or magnetic detector comprising Hall elements that utilize the Hall effect, coils for detecting a static magnetic field, magnetoresistance (MR) effect elements, or magnetic impedance (MI) effect elements. An example of using a magnetic detector for detecting magnetized substances in a non-magnetic product while not detecting non-magnetizable metal is disclosed in U.S. Pat. No. 5,923,165 to Horita et al. However, a magnetic detector is limited to detecting magnetized metals. It cannot detect non-magnetizable metals such as aluminum, copper, lead, non-magnetizable stainless steel, brass, and cast zinc. Since non-magnetizable metals from a plurality of sources can be present in the flesh of an animal during processing after slaughter, it is preferable that the detection means be able to detect both magnetizable and non-magnetizable metals in the flesh of an animal. Therefore, a metal detector is preferred. Thus, the detectable heavy duty magnetizable needle cannula of the present invention is compatible with metal detectors that detect both magnetizable and non-magnetizable metals such as aluminum, copper, lead, non-magnetizable stainless steel, brass, and cast zinc.

Figure 3:
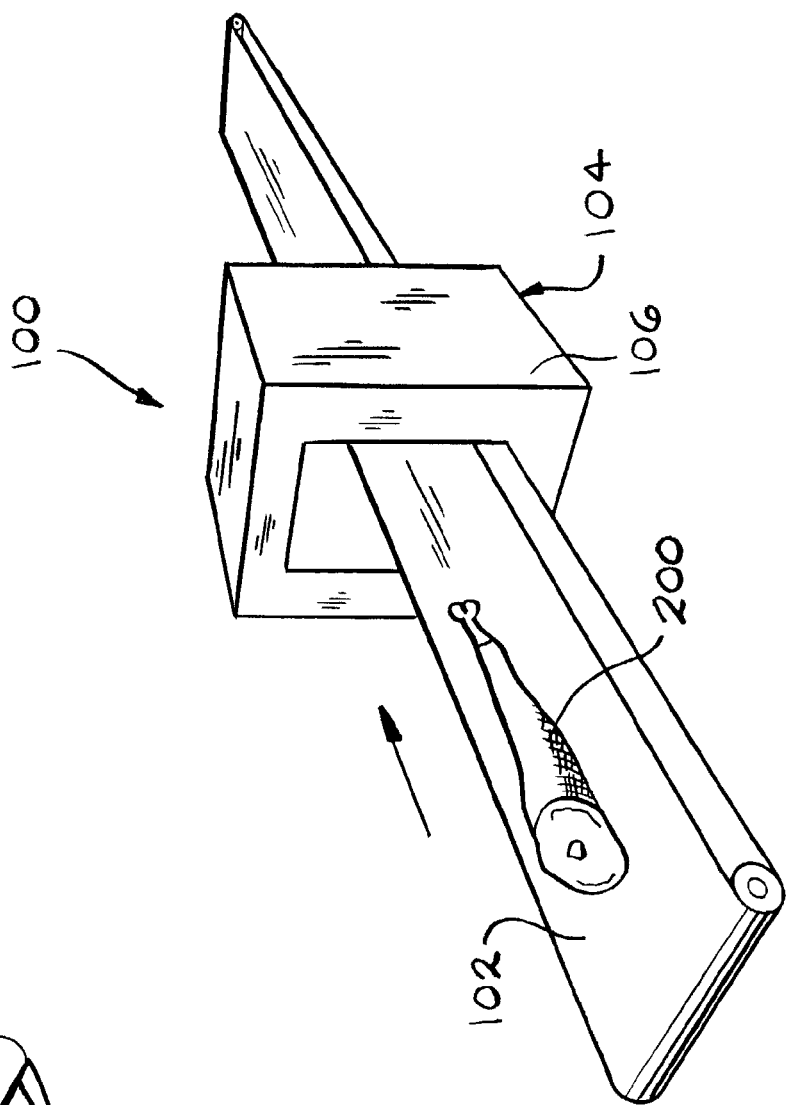
FIG. 3 is a perspective view of an apparatus comprising a metal detector for detecting a part of the detectable heavy duty needle of the present invention broken off in the flesh of an animal and a conveyor for transporting the flesh through the metal detector.
Figure 4:
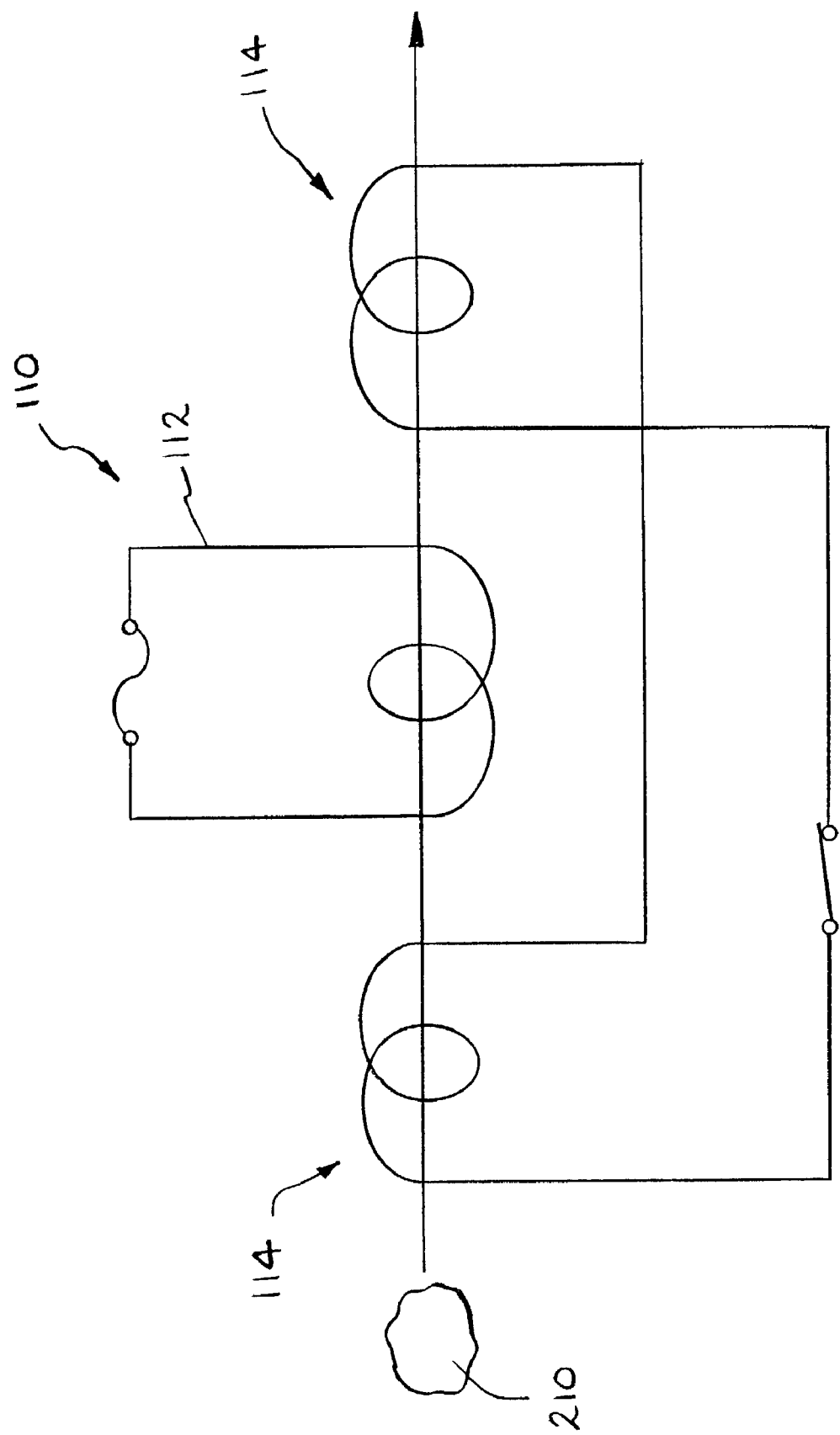
FIG. 4 shows a balanced three-coil system of a metal detector for use with the present invention.

FIG. 3 shows one embodiment for an apparatus for detecting metal in the flesh of an animal after slaughter. Shown is apparatus 100 comprising a conveyor means 102 for transporting animal flesh or meat products after slaughter 200 through metal detector 104 for detecting whether animal flesh contains a broken piece of needle cannula 12 of the present invention. Metal detector 104, comprises a coil arrangement 110 (shown in FIG. 4) inside a metal case 106. This metal detector embodiment is one that is commonly used in the meat processing industry to detect metal in animal flesh after slaughter. The metal detector 104 can be operably connected to a control unit (not shown) to signal when the animal flesh contains a broken part of the needle cannula of the present invention. The control unit can comprise a computer processing unit. The apparatus 100 can further comprise a means for removing from conveyor animal flesh or meat products after slaughter that contain a broken piece of the needle cannula of the present invention. Alternatively, apparatus 100 comprises a means for marking animal flesh or meat products after slaughter that contain the needle cannula of the present invention for removal from conveyor means 102 either manually or mechanically. In particular embodiments, apparatus 100 can further comprise a means for producing a high magnetic field (not shown) to magnetize or enhance the magnetism of the stainless steel comprising needle cannula 12 or piece thereof in animal flesh or meat product after slaughter 200 before it enters metal detector 104. This improves the detectability of the metal.

The metal detector preferably uses a balanced three-coil system 110 (FIG. 4), which is a configuration that is commonly used in the metal detectors used in the meat processing industry to detect metal in the flesh of animals after slaughter. The three coils are wound on a non-metallic frame or former, each exactly parallel with the other. The center transmitter coil 112 is connected to a high frequency radio transmitter. The two receiver coils 114 on each side of coil 112 act as radio receivers or aerials. Because receiver coils 114 are identical and the same distance to transmitter coil 112, they pick up the same signal and an identical voltage is induced in each. When coils 114 are connected in opposition, they cancel out resulting in zero output.

When a piece of metal in animal flesh or meat product after slaughter 210 passes through coil arrangement 110, the high frequency field is disturbed under one coil, changing the voltage generated by a few microvolts. The perfect state of balance is lost and the output is no longer zero. The resulting signal output is sent to a receiver where it is processed and amplified. The processed signal is then sent to a computer processing unit or other device. It is this frequency disturbance phenomenon that is used to detect the presence of unwanted metal in the flesh of an animal after slaughter. A magnetized or magnetic piece of metal will also induce a change in voltage that can be measured by the metal detector.

Preferably, coil arrangement 110 is mounted inside a metal case 106 with a hole in the center to allow passage of animal flesh or meat product after slaughter 200 (FIG. 3). Metal case 106 provides rigidity to coil arrangement 110 and acts as a screen, preventing prevent airborne electrical signals, or nearby metal items and machinery from disturbing the detector. Aluminum is frequently used for metal case 106 but where frequent washdown is required such as in meat processing plants, stainless steel is generally used.

When a non-spherical particle such as a part of a needle cannula passes through metal detector 104, it will be easier to detect in one orientation than in another. In the case of a linear non-ferrous article, the article is easily detected when the orientation of the article is perpendicular to its flow through the detector and difficult to detect when it is orientated parallel to the direction of flow through the detector. The converse is true for ferrous linear articles. However, this orientation effect is generally only evident when the diameter of the object is less than the spherical sensitivity of the metal detector. For example, when the sensitivity of the detector is set at 1.5 mm (0.06 inch) diameter, only articles thinner than 1.5 mm will show the orientation effect. Increasing the sensitivity to 1.0 mm, only articles thinner than 1.0 mm (0.04 inch) will show the orientation effect. But the ability to detect thin linear articles independent of orientation is very dependent on the composition of the article.

In general, linear non-magnetized ferrous articles with a diameter of 0.95 mm (0.037 inch), the minimum length to guarantee detectability at a sensitivity of 1.2 mm independent of orientation effects is 1.5 mm (0.06 inch). At a sensitivity of 1.5 mm, the minimum length that is guaranteed detectable is 3.0 mm (0.12 inch); at a sensitivity of 2.0 mm (0.08 inch), the minimum length is 6 mm (0.24 inch); and, at a sensitivity of 2.5 mm (0.1 inch) the minimum length that is guaranteed detectable is 11.0 mm (0.44 inch).

In contrast, a linear non-magnetized stainless steel article with a diameter of 1.60 mm (0.063 inch), the minimum length to guarantee detectability at a sensitivity of 1.5 mm independent of orientation effects is 8.0 mm (0.31 inch). At a sensitivity of 2.0 mm, the minimum length that is guaranteed detectable is 24 mm (0.96 inch), and at a sensitivity of 2.5 mm, the minimum length that is guaranteed detectable is 64.0 mm (2.52 inch). However, at a sensitivity of 1.2 mm, a stainless steel article with a diameter of 1.6 mm is not detectable independent of orientation effects. Thus, it is much more difficult to guarantee detection of a stainless steel article than a ferrous article. The orientation effect is of particular significance in the meat processing industry because the orientation of a broken stainless steel needle cannula in the flesh of the meat from an animal is unknown.

While the sensitivity of the metal detector can be increased in order to detect short articles of small diameter, other problems become manifest. For example, as sensitivity is increased, the problems of drift become more acute and the number of false rejects can increase to an unacceptable level. Also, wet products such as meat products create an interference signal in the detector, which must be canceled out. This tends to reduce the sensitivity of the detector. To minimize the effect, a lower operating frequency is often selected in the range of 10 to 50 KHz. This reduces the interference signal from the wet product but also reduces the sensitivity of the detector, particularly as it pertains to stainless steel.

Thus, in order to detect a length of a stainless steel 16 gauge prior art needle cannula, which has a diameter of about 1.65 mm, the length of needle that is embedded in the flesh of the animal must be at least about 8 mm to be detected free of orientation effects at a sensitivity of 1.5 mm or at least about 24 mm to be detected free of orientation effects at a sensitivity of 2.0 mm. The standard 16 gauge needle used for injecting animal health products into an animal is about 19.0 mm in length.

In contrast, the length of the magnetized heavy duty stainless steel needle cannula of the present invention that can be detected free of orientation effects at a sensitivity of 1.5 mm and 2.0 is about 7.0 mm and 21.0 mm, respectively. Furthermore, because the needle is magnetic, the length of the needle that is detectable free of orientation effects is shorter still. Thus, the magnetic heavy duty stainless steel needle cannula of the present invention can be detected free of orientation effects at a sensitivity that is about equivalent to the detectability of a linear ferrous article. Therefore, the detectable heavy duty needle of the present invention reduces the risk that a meat product containing a part of a broken needle cannula will escape detection.

The apparatus 100 can comprise one or more magnetic detectors disposed over the conveyor such as those comprising Hall elements, coils, MR effect elements, or MI effect elements. When a piece of magnetized metal passes through Hall elements or coils it causes a measurable variation in voltage, when it passes through MR effect elements it causes a measurable variation in resistance, and when it passes through MI effect elements it causes a measurable variation in resistance. The measurable variation produces a signal that is sent to a control unit as above, which directs the removal of the meat containing the magnetized metal. While a magnetic detector can be the sole detection means in the apparatus, it is preferable that the apparatus comprise a metal detector to enable detection of non-magnetizable metals. An apparatus comprising solely a magnetic detector is limited to detecting magnetic metals or metals that can be magnetized to possess a residual magnetism.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

I claim:
1. A needle assembly comprising an elongate permanently magnetic or magnetizable stainless steel needle cannula having a proximal end, a distal end and a sidewall therebetween, a gauge of the needle cannula having an outer diameter and a lumen with a lumen diameter,
   wherein:
   (i) the outer diameter between the proximal end and the distal end is greater than an outer diameter of a standard needle cannula;
   (ii) the lumen diameter is identical to a lumen diameter of the standard needle cannula;
   (iii) the standard needle cannula is between 14 and 27 gauge;
   (iv) the cannula at its proximal end is securely fixed to a mounting hub which is capable of being mounted on a device operable for injecting a dosage of a material in to the flesh of an animal;
   (v) the magnetic or magnetizable stainless steel needle cannula has a sidewall thickness which is larger than that of the standard needle cannula with the lumen diameter and increases detectability in a metal detector over the standard needle cannula such that the magnetism and the sidewall thickness enables detection of the magnetism of the needle cannula or piece thereof in the flesh of the animal upon slaughter and processing into a food if the needle cannula or piece thereof were to break off in the flesh of the living animal during the injection; and

(vi) the magnetic or magnetizable stainless steel comprises 0.003-0.01 wt. % Al.

2. The needle assembly of claim 1 wherein the magnetic or magnetizable stainless steel comprises Fe and 0.36 wt % Si, less than 0.03 wt % P, 24.68 wt % Cr, 0.01 wt % Al, 0.90 wt % Mn, 0.009 wt % S, 1.80 wt % Mo, less than 0.01 wt % Ti, 0.08 wt % C, 4.98 wt % Ni, 0.10 wt % Cu, and less than 0.01 wt % Pb.

3. The needle assembly of claim 1 or 2 wherein the assembly is for use in a hypodermic needle and the device is a hypodermic syringe.

4. The needle assembly of claim 1 or 2 wherein the sidewall has a thickness greater than 0.46 mm with the lumen having a diameter of about 1.19 mm.

5. The needle assembly of claim 4 wherein the sidewall has a thickness of 0.64 mm.

6. The needle assembly of claim 1 or 2 wherein the needle cannula has a circular cross-section.

7. The needle assembly of claim 1 or 2 wherein the mounting hub includes projections extending therefrom for threaded engagement with a luer collar.

8. The needle assembly of claim 1 wherein the magnetic or magnetizable stainless steel comprises 0.9-1 wt. % Mn.

9. A stainless steel tubular needle defined by at least one wall forming the tube as a cannula supported on a hub for mounting on a device operable for injecting a dosage of a material in to the flesh of an animal, a gauge of the needle cannula having an outer diameter and a lumen with a lumen diameter,
wherein:
(i) the outer diameter between the proximal end and the distal end is greater than an outer diameter of a standard needle cannula;
(ii) the lumen diameter is identical to a lumen diameter of the standard needle cannula;
(iii) the standard needle cannula is between 14 and 27 gauge;
(iv) the stainless steel needle is permanently magnetic or magnetizable;
(v) the needle cannula has a sidewall thickness which is larger than that of the standard needle cannula with the lumen diameter and increases detectability in a metal detector over the standard needle cannula such that the magnetism and the sidewall thickness enables detection of the magnetism of the needle cannula or piece thereof in the flesh of the animal upon slaughter and processing into a food if the needle cannula or piece thereof were to break off in the flesh of the living animal during the injection; and
(vi) the magnetic or magnetizable stainless steel comprises 0.003-0.01 wt. % Al.

10. The stainless steel tubular needle of claim 9 wherein the stainless steel contains Fe and 0.36 wt % Si, less than 0.03 wt % P, 24.68 wt % Cr, 0.01 wt % Al, 0.90 wt % Mn, 0.009 wt % S, 1.80 wt % Mo, less than 0.01 wt % Ti, 0.08 wt % C, 4.98 wt % Ni, 0.10 wt % Cu, and less than 0.01 wt % Pb.

11. The needle of claim 9 or 10 which is a hypodermic needle and wherein the material is a fluid.

12. The needle of claim 9 or 10 wherein each wall has a thickness greater than 0.46 mm and wherein the needle has an inside diameter of about 1.19 mm.

13. The needle assembly of claim 12 wherein the wall has a thickness of 0.64 mm.

14. The needle of claim 9 or 10 with a circular cross-section.

15. The stainless steel tubular needle of claim 9 wherein the magnetic or magnetizable stainless steel comprises 0.9-1 wt. % Mn.

16. The needle assembly of claim 1 or 9 wherein the stainless steel comprises Fe and 0.01-3.0 wt % Si, less than 0.03 wt % P, 4-25 wt Cr, 0.01-1.0 wt % Mn, 0.001-0.03 wt % S, 0.01-5.0 wt % Mo, 0.01-1.0 wt % Ti, 0.003-0.08 wt % C, 0.01-5.0 wt % Ni, 0.01-0.5 wt % Cu, less than 0.01 wt % Pb, 0.02-0.5 wt % Bi, 0.5-1.0 wt % Nb, 0.02-1.0 wt % Zr, and 0.05-1.0 wt % V.

17. A needle assembly comprising an elongate permanently magnetic or magnetizable stainless steel needle cannula having a proximal end, a distal end and a sidewall therebetween, the cannula having a lumen therethrough wherein the cannula at its proximal end is securely fixed to a mounting hub which is capable of being mounted on a device operable for injecting a dosage of a material in to the flesh of an animal,
wherein:
(i) the magnetic or magnetizable stainless steel composition is a UNS S32900 stainless steel;
(ii) a gauge of the needle cannula has an outer diameter and a lumen with a lumen diameter;
(iii) the outer diameter between the proximal end and the distal end is greater than an outer diameter of a standard needle cannula;
(iv) the lumen diameter is identical to a lumen diameter of the standard needle cannula;
(v) the standard needle cannula is between 14 and 27 gauge;
(vi) the needle cannula has a sidewall thickness which is larger than that of the standard needle cannula with the lumen diameter and increases detectability in a metal detector over the standard needle cannula such that the magnetism and the sidewall thickness enables detection of the magnetism of the needle cannula or piece thereof in the flesh of the animal upon slaughter and processing into a food if the needle cannula or piece thereof were to break off in the flesh of the living animal during the injection; and
(vii) the magnetic or magnetizable stainless steel comprises 0.003-0.01 wt. % Al.

18. The needle assembly of claim 17 wherein the magnetic or magnetizable stainless steel comprises 0.9-1 wt. % Mn.

* * * * *

UNITED STATES PATENT AND TRADEMARK OFFICE
CERTIFICATE OF CORRECTION

Page 1 of 1

PATENT NO.         : 7,905,869 B2
APPLICATION NO.    : 10/215339
DATED              : March 15, 2011
INVENTOR(S)        : Gordon Prindle It is certified that error appears in the above-identified patent and that said Letters Patent is hereby corrected as shown below:

Column 2, line 27 -- an animals -- should be -- an animal --

Column 5, line 49 -- permanent magnetic -- should be -- permanent magnet --

Column 7, line 1 -- prevent -- should be removed

Signed and Sealed this
Fourth Day of September, 2012

David J. Kappos
*Director of the United States Patent and Trademark Office*